US007098375B2

(12) United States Patent
Edlund et al.

(10) Patent No.: US 7,098,375 B2
(45) Date of Patent: Aug. 29, 2006

(54) ANIMAL AND CELL MODELS FOR TYPE II DIABETES AND THEIR USE

(75) Inventors: Helena Edlund, Umeå (SE); Alan Hart, Cardrona (GB); Nathalie Baeza, Lyon Cedex (FR); Åsa Apelqvist, Stanford, CA (US)

(73) Assignee: Betagenon AB, Stockholm (SE)

( * ) Notice: Subject to any disclaimer, the term of this patent is extended or adjusted under 35 U.S.C. 154(b) by 403 days.

(21) Appl. No.: 10/257,155

(22) PCT Filed: Apr. 6, 2001

(86) PCT No.: PCT/SE01/00783

§ 371 (c)(1),
(2), (4) Date: Oct. 7, 2002

(87) PCT Pub. No.: WO01/76361

PCT Pub. Date: Oct. 18, 2001

(65) Prior Publication Data

US 2003/0056240 A1    Mar. 20, 2003

(30) Foreign Application Priority Data

Apr. 7, 2000    (SE)    .................................. 0001285

(51) Int. Cl.
*A01K 27/027*    (2006.01)
*A01K 67/033*    (2006.01)
(52) U.S. Cl. .............................. 800/18; 800/13; 800/21
(58) Field of Classification Search ............... 800/3–21
See application file for complete search history.

(56) References Cited

OTHER PUBLICATIONS

Kappell et al, 1992, Current Opinion in Biotechnology vol. 3, 548-53.*
Mullins et al 1993, Hypertension vol. 22, p. 630-3.*
Hammer et al, J Anim Sci 1986;63:269-78.*
Houdebine 1994, J. Biotech. 34, p. 269-87.*
Wall 1996, Theriogenology 45, 57-68.*
Wall et al, J Diary Sci 1997;80:2213-24.*
Mullins et al 1996, J. Clin. Invest. 98, p. S37-40.*
Cameron 1997, Molec. Biol. 7, p. 253-65.*
Sigmund 2000, Arterioscler. Throm. Vasc. Biol. 20, p. 1425-9.*
Niemann 1998, Transg. Res. 7, p. 73-5.*
Jackson et al, J Cell Sci 1997;100:1261-8.*
Rousseau et al, Exp Eye Res 2000;71:395-404.*
Werner et al, Mole Cell Biol 1992;12:82-88.*
Logan and Sharma, Clin Exp Pharmacol Physiol Dec. 1996;26:1020-25.*
Ahlgren et al., (1998) "Beta-Cell-specific inactivation of the mouse Ipf1/Pdx1 gene results in loss of the Beta-cell phenotype and maturity onset of diabetes", *Genes & Development*, 12:1763-1768.
Apelqvist et al., (1999) "Notch signalling controls pancreatic cell differentiation", *Nature*, 400:877-881.
Apelqvist et al., (1997) "Sonic hedgehog directs specialised mesoderm differentiation in the intestine and pancreas", *Current Biology*, 7:801-804.
Celli et al., (1998) "Soluble dominant-negative receptor uncovers essential roles for fibroblast growth factors in multi-organ induction and patterning", *EMBO Journal*, 17:1642-1655.
Edlund H., (2001) "Factors controlling pancreatic cell differentiation and function", *Diabetologia*, 44:1071-1079.
Edlund H., (1998) "Transcribing Pancreas", *Diabetes*, 47:1817-1823.
Hart et al., (2000) "Attenuation of FGF signalling in mouse Beta-Cells leads to diabetes", *Nature*, 408:864-868.
Hostens et al., (1999) "Exposure of human islets to cytokines can result in disproportionately elevated proinsulin release", *J. of Clin. Invest.*, 104:67-72.
Hughes S., (1997) "Differential Expression of the Fibroblast Growth Factor Receptor (FGFR) Multigene Family in Normal Human Adult Tissues", *J. of Histochemistry & Cytochem.*, 45:1005-1019.
Jonsson et al., (1994) "Insulin-promoter-factor 1 is required for pancreas development in mice", *Nature*, 371:606-609.
Li et al., (2001) "Persistent expression of Hlxb9 in the pancreatic epithelium impairs pancreatic development", *Dev. Bio.*, 240:247-253.
Ohlsson et al., (1993) "IPF1, a homeodomain-containing transactivator of the insulin gene", *EMBO Journal*, 12:4251-4259.
Ritz-Laser et al., (2002) "The pancreatic beta-cell-specific transcription factor Pax-4 inhibits glucagon gene expression through Pax-6", *Diabetologia*, 45:97-107.
Tingstedt et al., (1999) "Gastric Amylin Expression: Cellular Identity and Lack of Requirement for the Homeobox Protein PDX-1. A Study in Normal and PDX Deficient Animals with a Cautionary Note on Antiserum Evaluation", *J. of Histochem. & Cytochem.*, 47:973-980.

\* cited by examiner

*Primary Examiner*—Q. Janice Li
(74) *Attorney, Agent, or Firm*—Darby & Darby

(57) ABSTRACT

A transgenic diabetes type II model laboratory animal is disclosed which comprises β-cells expressing a dominant negative form (dnFGFR1c) of FGFR1c. Also disclosed is the use of the Ipf1/pdx1 promoter for controlling expression of FGFR1c; β-cells in which the expression of PC1/3 is down-regulated or absent or which are competent to express a dominant negative form (dnFGFR1c) of FGFR1c; mature β-cells incompetent to express Glut2 or in which the processing of proinsulin is substantially impaired; a method of preventing or treating type II diabetes.

4 Claims, 9 Drawing Sheets

US 7,098,375 B2

ANIMAL AND CELL MODELS FOR TYPE II DIABETES AND THEIR USE

Figure 1:
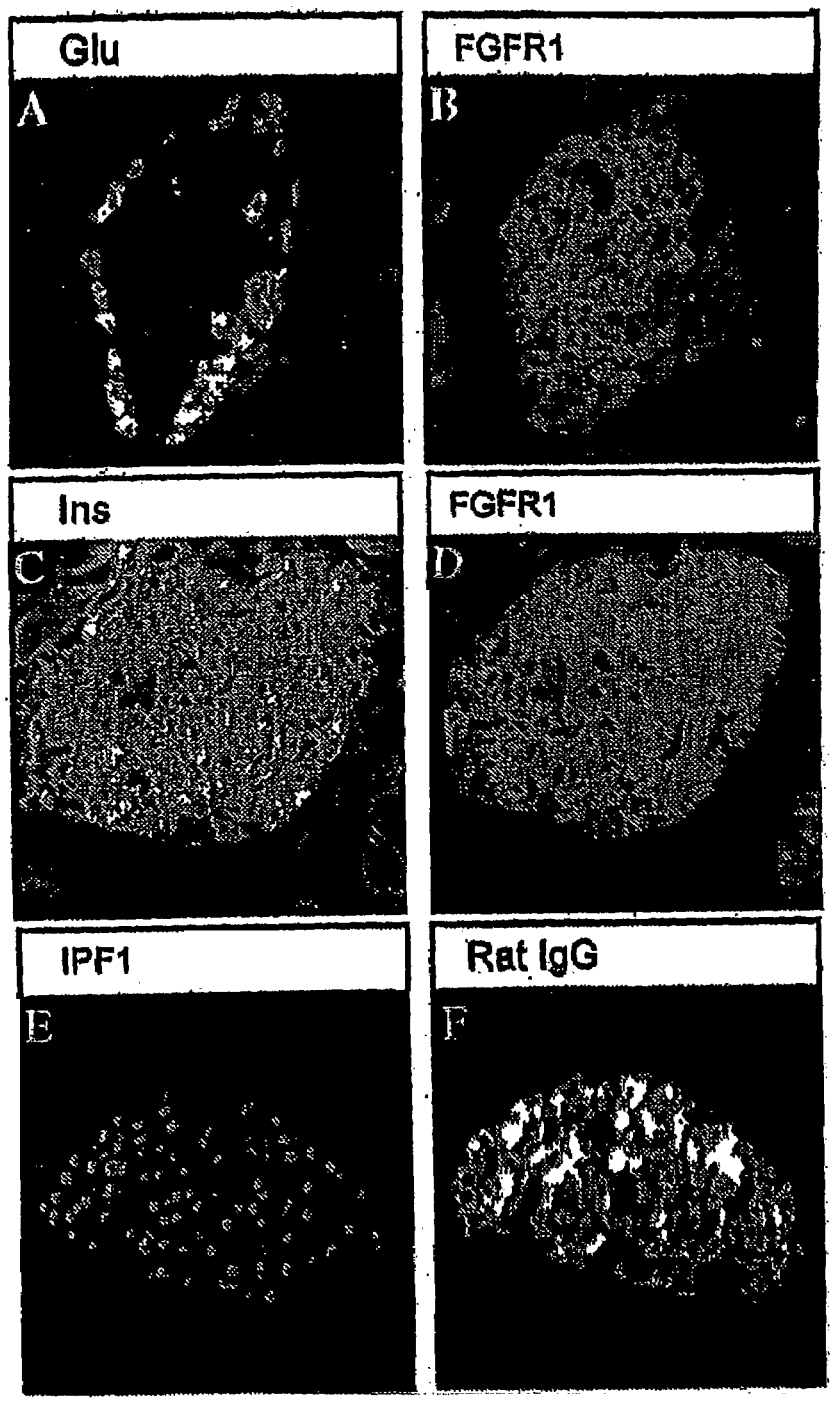

This is a U.S. national phase application under 35 U.S.C. §371 of International Patent Application No. PCT/SE01/00783, filed Apr. 6, 2001, and claims the benefit of Swedish Patent Application No. 0001285-6, filed Apr. 7, 2000. The International Application was published in English on Oct. 18, 2001 as WO 01/76361 A1 under PCT Article 21(2).

FIELD OF THE INVENTION

The present invention relates to an animal model for type II diabetes, in particular a transgenic mouse, in which the expression of fibroblast growth factor receptors essential for ensuring a functional β-cell identity is perturbed. The invention also relates to the use of this model for studying type II diabetes, in particular with the aim of developing therapies therefore. The invention also relates to a corresponding cells and their components useful as in-vitro or in-vivo models. Furthermore the invention relates to a method of preventing or treating diabetes type-II.

BACKGROUND OF THE INVENTION

The Fibroblast Growth Factor (FGF) gene superfamily is a family of conserved, secreted proteins that have been shown to play a critical role in many biological processes (Kato and Sekine, 1999; Szebenyi and Fallon, 1999). FGF-signalling is achieved by binding of the ligand, FGF, to the extra-cellular domain of high affinity membrane bound FGFR, which belongs to the tyrosine kinase family of receptors (Kato and Sekine, 1999; Szebenyi and Fallon, 1999). Today around 20 different FGF genes and 4 different FGFR genes have been identified, and multiple ligands can interact with one and the same receptor (Kato and Sekine, 1999; Szebenyi and Fallon, 1999). The level of complexity of signalling via these receptors is further compounded by the fact that alternative splice variants exist for these receptors. Loop three of the extracellular domain (=ligand binding domain) can splice to give rise to b, or c, isoform. This isoform variation ultimately determines ligand specificity and proper ligand-receptor interaction ultimately leads to activation of the intracellular tyrosine kinase domain (Kato and Sekine, 1999; Szebenyi and Fallon, 1999).

FGF-signalling has been implicated in a variety of distinct biological processes including patterning, differentiation, morphogenesis, proliferation, survival, angiogenesis, tumorogenesis, etc. (Kato and Sekine, 1999; Szebenyi and Fallon, 1999). In mouse, an early embryonic lethality or functional redundancy have, however, largely hampered direct genetic approaches aiming at elucidating the role of FGF-signalling during development and in the adult. Thus these approaches has for the most part failed to provide critical information regarding the role of FGF-signalling during later stages of vertebrate organogenesis, including the pancreas. An alternative approach have been to impair FGF-signalling via organ specific expression of dominant negative forms of FGFR that will competitively block FGF signalling via the endogenous, corresponding FGFR variant. This approach has been successfully used to antagonise FGF-signalling in a number of different systems.

Viral infection of a dominant negative FGFR1 construct in chick limb muscle mass blocked the differentiation of myoblast to myotubes providing evidence that this process depends on FGF-signalling (Itoh et al., 1996). Studies focused on maintenance of cell types within the retina revealed that expression of dnFGFR2 under the control of the bovine rhodopsin promoter increased photoreceptor degeneration (Campochiaro et al. 1996). The specificity of dominant negative constructs with respect to ligand binding was demonstrated in analyses where dnFGFR1c and dnFGFR2b constructs where expressed in transgenic mice using the mammary tumour virus promoter (Jackson et al.,1997). Expression of dnFGFR1c under these conditions did not result in any discernible phenotype whereas an impairment of lobuloalveolar development in the mammary gland was observed when using the dnFGFR2b variant (Jackson et al.,1997). Moreover, FGF8 mediated induction of dopaminergic (DA) neurons was successfully inhibited when growing six somite rat ventral mid/hindbrain explants in presence of soluble dnFGFR3c, i.e. the high-affinity blocking receptor for FGF8 (Ye et al., 1998). In contrast, when the same experiment was performed using soluble, dnGFGR1c, a low-affinity nonblocking receptor for FGF8, DA neurons readily appeared (Ye et al., 1998). Together these analyses demonstrate the effectiveness by which FGF signalling, in an apparent ligand-specific manner, can be perturbed using a dominant-negative FGFR approach.

Three different FGF-signalling mutant mice, involving transgenic approaches to over-express either a ligand or a dn form of a receptor, resulting in a pancreatic phenotypes have been reported. Transgenic over-expression of FGF7/KGF in the mouse liver induced pancreatic ductal hyperplasia (Nguyen et al. 1996) and similarly, transgenic mice with forced expression of FGF-7/KGF in pancreatic β-cells under the control of the insulin promoter show enlarged islets containing proliferating duct cells (Krakowski et al., 1999). General transgenic over-expression of dnFGFR2b under the control of the metallothionein promoter resulted in pancreatic hypoplasia (Celli et al. 1998). Together these studies indicate that signalling through FGFR2b may operate during pancreatic development. In vitro experiments involving culturing of pancreatic rudiments support such a scenario and suggest that FGFs positively stimulate pancreatic epithelial cell proliferation and exocrine cell differentiation (Le Bras et al. 1998, Miralles et al. 1999).

Selective inactivation of the IIIb form of FGFR2 leads to developmental abnormalities in limbs, lung, anterior pituitary, salivary glands, inner ear, teeth and skin but apparently not in the pancreas (De Moerlooze et al., 2000). Thus, the roles of FGFR2b during pancreas development remain to be determined.

Failure of the β-cell to compensate for an increased demand for insulin is a key feature in the manifestation of type 2 diabetes. Type 2 diabetes is the most common form of diabetes, affecting 2–3% of the world-wide population, and is the combined result of resistance to insulin action coupled with a defect in β-cell compensation (Kahn, 1998; Kahn and Rossetti, 1998; Taylor, 1999). The molecular defects underlying the development of the disease are not fully understood and there are also uncertainties as to what is the primary defect initiating the disease; the insulin resistance or the β-cell failure. A typical trait associated with the disease is the increased proinsulin to insulin (P/I) ratio observed in many type 2 diabetic patients (Porte and Kahn, 1989). The relationship between the increased P/I ratio and the etiology of the disease has however remained diffuse; i.e. is it a consequence rather than a directly contributing factor to the disease? Several independent studies points towards an increased P/I ratio being an early sign of primary β-cell dysfunction, independent of insulin resistance, which is directly associated with the conversion from a prediabetic to an overt diabetic state over a short time period (Mykkänen et al., 1995; Kahn et al., 1995, Nijpels et al., 1996; Rachman et al., 1997; Mykkänen et al., 1997; Haffner et al 1997; Larsson and Ahrén, 1999). Moreover, it has been suggested that normal β-cells respond to an increased insulin resistance by enhanced processing of insulin and that the increased P/I ratio in individuals with an impaired glucose tolerance, and/or type 2 diabetes, is the consequence of defects in proinsulin processing (Mykkänen et al., 1997, Larsson and Ahrén, 1999).

Processing of proinsulin to insulin in β-cells is catalysed by the sequential actions of prohormone convertases PC1/3 and PC2, which both act in concert with carboxpeptidase E (CPE) (FIG. 7) Analyses of PC2 null mutant mice demonstrated a crucial role for PC2 in the processing of proglucagon and prosomatostatin in α- and δ- cells, respectively (Furuta et al., 1998). Proinsulin processing in β-cells was less affected in the PC2 null mutant mice providing evidence that PC3 is quantitatively more important than PC2 with respect to processing of proinsulin to active insulin (Furuta et al., 1998). At present there is a lack of genetically defined animal models that mimic these aspects of human type 2 diabetes. The importance of this disease in terms of human suffering and health care costs makes the provision of such a model an important goal.

OBJECTS OF THE INVENTION

It is an object of the present invention to provide an animal model which mimics human type II diabetes and which can be used to develop a therapy.

It is another object of the invention to provide a method of preventing or treating type II diabetes.

Further objects of the invention will become evident from the study of the following short description of the invention and preferred embodiments thereof, the figures illustrating the invention, and the appended claims.

SUMMARY OF THE INVENTION

The invention is based on the insight that, in addition to the previously reported expression of FGFR2b during pancreas development, FGFR2 and FGFR1 are both expressed in the adult β-cell. In regard of FGFR1, a functional role was demonstrated by impairing signalling through FGFR1c via the expression of a dominant negative form of this receptor, dnFGFR1c (Ye et al., 1998), under control of the Ipf1/Pdx1 promoter (Apelqvist et al., 1997).

Mice expressing the dnFGFR1c exhibit a grossly normally developed pancreas with no apparent abnormalities but develop diabetes with age. The expression of dnFGFR1c in β-cells results in disorganised islets with reduced numbers of β-cells displaying an apparent immature molecular identity. First, the β-cells do not express detectable of levels Glut2 which is one of the key components of the glucose sensing machinery. Secondly, the expression of one of the proinsulin processing enzymes, PC1/3, is impaired. Third, although insulin is synthesised by the β-cells it fails to be fully processed and remains largely in the form of proinsulin and/or partially processed.

According to the present invention, evidence is provided that the expression of FGFR1 is dependent on Ipf1/Pdx1 expression. Rip1/Ipf1$^{568}$ mice in which Ipf1/Pdx1 has been inactivated selectively in β-cells display disorganised islets and develop diabetes due to decreased insulin expression combined with a loss of Glut2 expression (Ahlgren et al., 1998). The expression of both FGFR 1 is down-regulated in the Rip1/Ipf1▲ mice suggesting that Ipf/Pdx1 is required for expression of FGFR1 and FGFR2 in β-cells. Moreover, in the Rip1/Ipf1▲ mice, alike in the Ipf1/dnFGFR1c mice, PC1/3 expression is impaired. These results suggest that signalling via FGFR1c is required for ensuring a correct number of β-cells and their proper function. Moreover, the results provide evidence that Ipf1/Pdx1 controls many aspects of the β-cell glucose homeostasis machinery, in part, by being required for the expression of FGFR1 in the β-cell.

In humans, heterozygosity for a nonsense mutation in the Ipf1 gene, which results in a dominant negative frameshift, has been linked to Maturity-Onset Diabetes of the Young (MODY) 4 [Stoffers et al., 1997], a monogenetic form of diabetes that results from β-cell dysfunction rather than insulin resistance. Moreover, missense mutations in the human Ipf1 gene are implicated in predisposing an individual to type 2 diabetes [Macfarlane et al., 1999; Hani et al., 1999]. Previous work has shown that Ipf1/Pdx1 is required for ensuring normal levels of insulin and Glut2 expression [Ohlsson et al., 1993; Ahlgren et al., 1998]. According to the present invention, as explained above, there is now genetic evidence suggesting that Ipf1/Pdx1 acts upstream of FGF-signalling in the β-cell, since genetic inactivation of Ipf1/Pdx1 in β-cells, as in the RIP1/Ipf1$^\Delta$ mice [Ahlgren et al., 1998], leads to reduced expression levels of FGFR1, and the ligands FGF1, FGF2, FGF4 and FGF5. Consequently, the RIP1/Ipf1$^\Delta$ mice also display reduced expression of PC1/3 paralleled by an increase in proinsulin in the β-cells of these mice.

The phenotypes observed in the FRID1 mice, i) reduced β-cell number, ii) loss of Glut2 expression leading to impaired glucose sensing and, iii) perturbed proinsulin processing due to the down regulation of prohormone convertase ⅓ and 2 expression [6], are reflective of the β-cell dysfunction associated with type 2 diabetic patients [Porte et al., 1989; Hales, 1994; Mykkanen et al., 1995; Mykkanen et al., 1999; Kahn et al., 1995; Kahn et al., 1995 bis; Larsson et al., 1999; Nijpels et al., 1996; Rachman et al., 1997; Haffner et al., 1997]. These findings suggest that signalling via FGFR1c may represent one factor required for β-cell expansion both during early life and in response to hyperglycaemia. Morover these data provide evidence that FGFR1c-signalling in the β-cell is required to ensure normal expression of key components in glucose sensing (Glut2) and insulin processing machinery (PC1/3 and PC2) and thus to maintain normoglycaemia. Last the analyses of the RIP1/Ipf1$^\Delta$ mice provide genetic evidence that that the IPF1/PDX1 transcription factor acts upstream of FGFR1-signalling in controlling key aspects of β-cell identity. The apparent conservation of Ipf1/Pdx1 gene function from mice to humans suggest that also the downstreams effects controlled by Ipf1/Pdx1 gene activity may be conserved [Stoffers et al., 1997; Macfarlane et al, 1999; Hani et al., 1999; Ohlsson et al., 1993; Ahlgren et al., 1998]. This strongly suggests that that FGF-signalling is important for β-cell function also in humans and that pertubation of this signalling pathway in adult human β-cells is linked to type II diabetes.

According to the present invention thus is disclosed a transgenic diabetes type II model laboratory animal comprising β-cells expressing a dominant negative form (dnFGFR1c) of FGFR1c. In particular the transgenic animal is a mouse.

According to the present invention is also disclosed the use of the Ipf1/Pdx1 promoter for controlling the expression of FGFR1c.

According to a first preferred aspect of the invention are disclosed β-cells in which the expression of PC1/3 is down-regulated or absent. Preferably the β-cells are comprised by an adult pancreas.

According to a second preferred aspect of the invention are disclosed β-Cells competent to express a dominant negative form (dnFGFR1c) of FGFR1c. Preferably the β-cells are comprised by an adult pancreas.

According to a third preferred aspect of the invention are disclosed mature β-cells incompetent to express Glut2. Preferably the β-cells are comprised by an adult pancreas.

According to a fourth preferred aspect of the invention are disclosed mature β-cells in which the processing of proinsulin to insulin is substantially impaired. In these cells levels of proinsulin convertase 1/3 are substantially reduced in comparison with the levels in non-transgenic mice. Preferably these β-cells are comprised by an adult pancreas.

According to a fifth preferred aspect of the invention are disclosed a reduced number of β-cells and a failure of β-cells to respond to hyperglycemia by replication.

In the following the invention will be by described in more detail by reference to preferred but not limiting embodiments.

SHORT DESCRIPTION OF THE FIGURES

Figure 2:
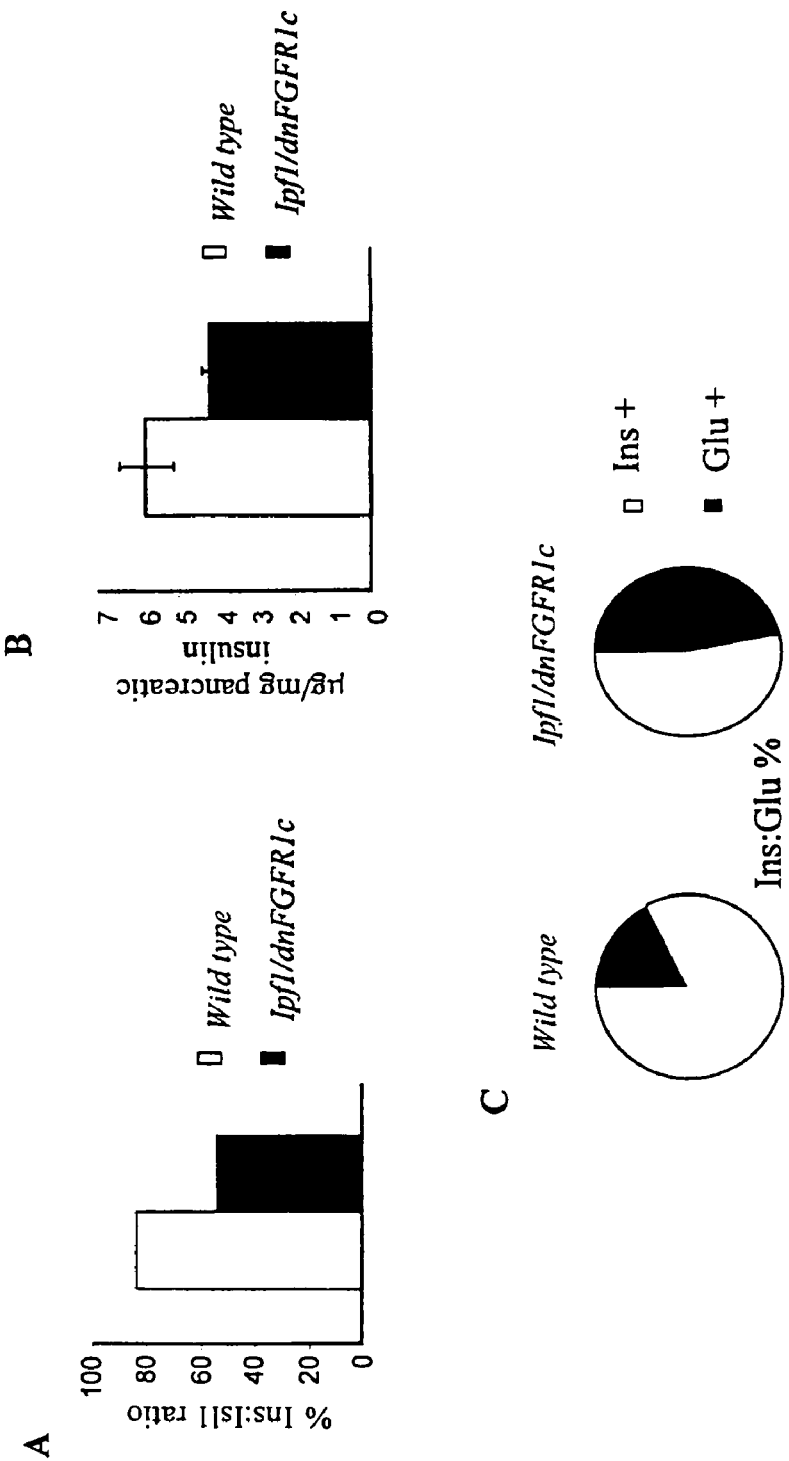
Figure 3:
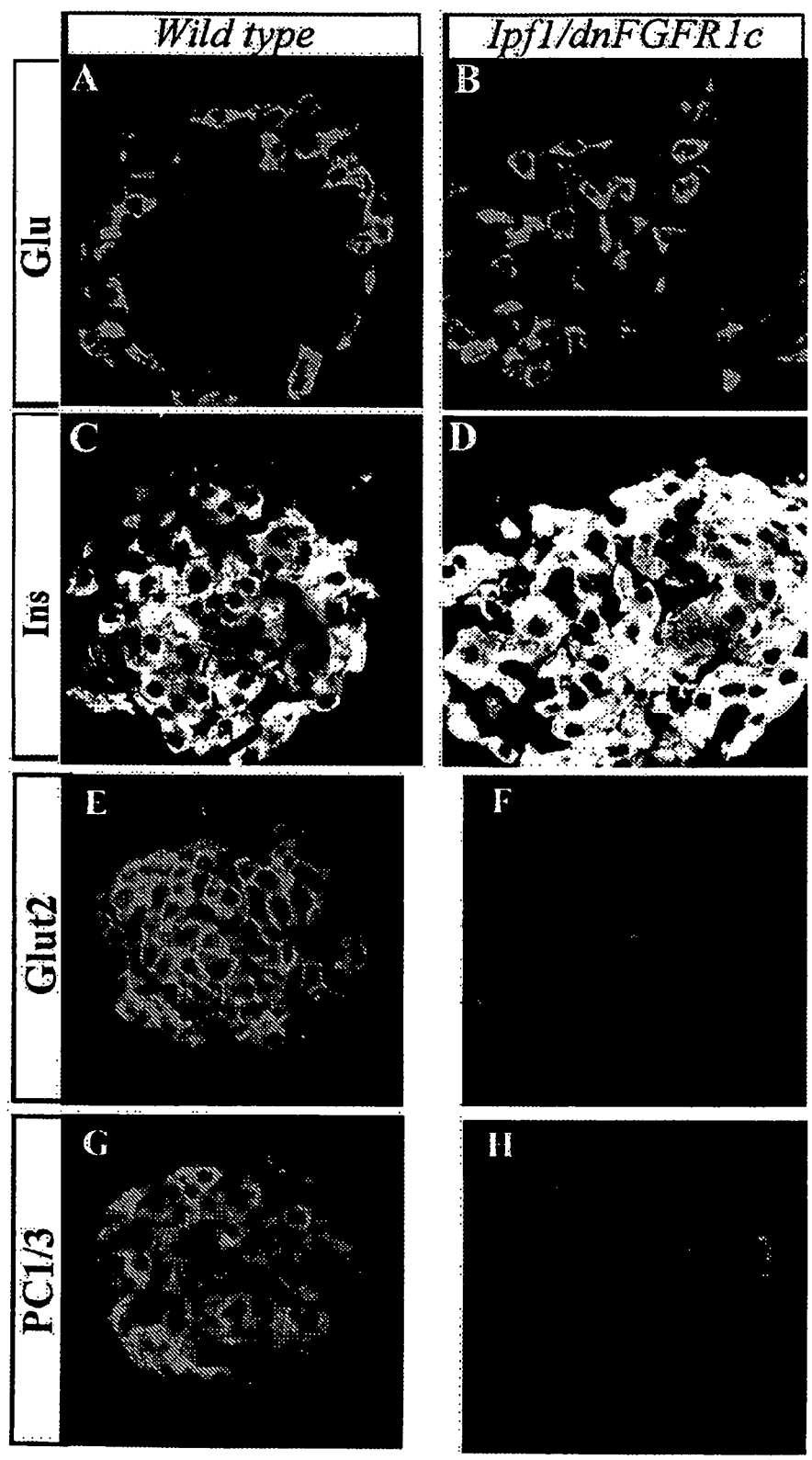
Figure 4:
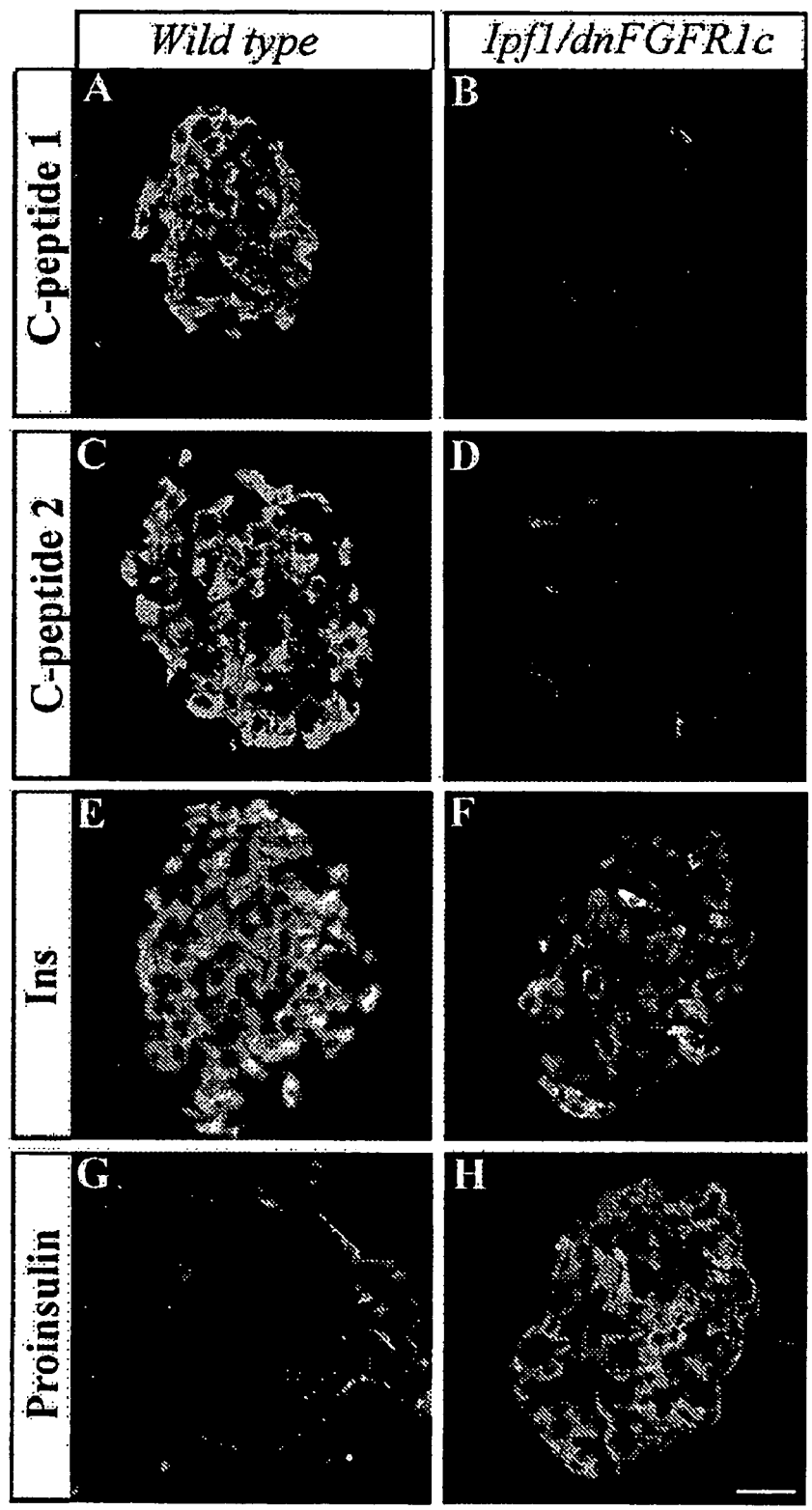
Figure 5:
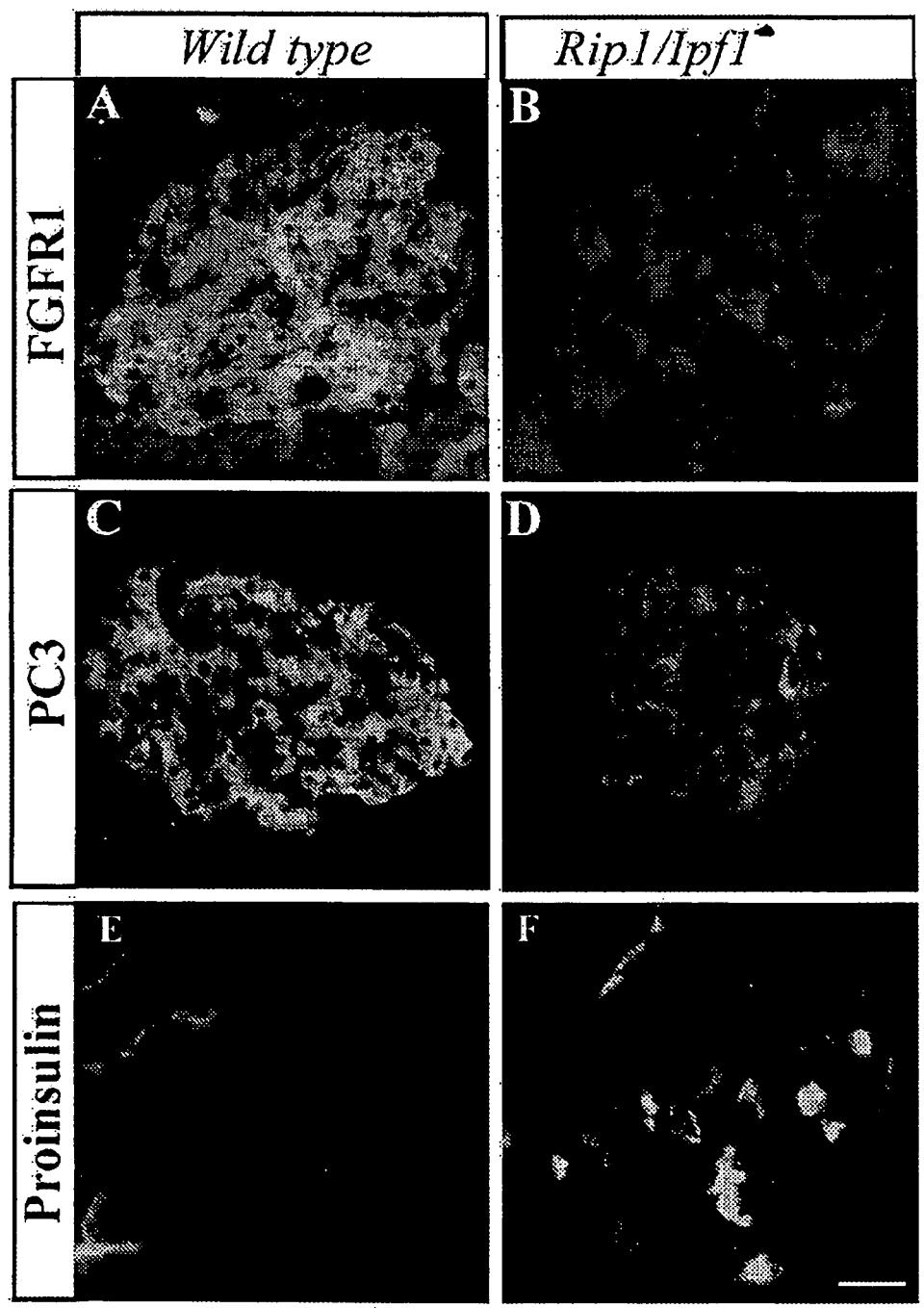

The preferred embodiments are illustrated by a number of figures showing:

FIG. 1 expression of FGFR1 in adult β-cells;

FIG. 2 reduction in number of ins$^+$-cells in Ipf1/dnFGFR1c mice;

FIG. 3 defects in β-cell identity in Ipf1/dnFGFR1c mice;

FIG. 4 impaired pro-insulin processing in Ipf1/dnFGFR1c mice;

FIG. 5 control by pf1/Pdx1 of multiple aspects of β-cell identity including FGFR1 expression.

Figure 6:
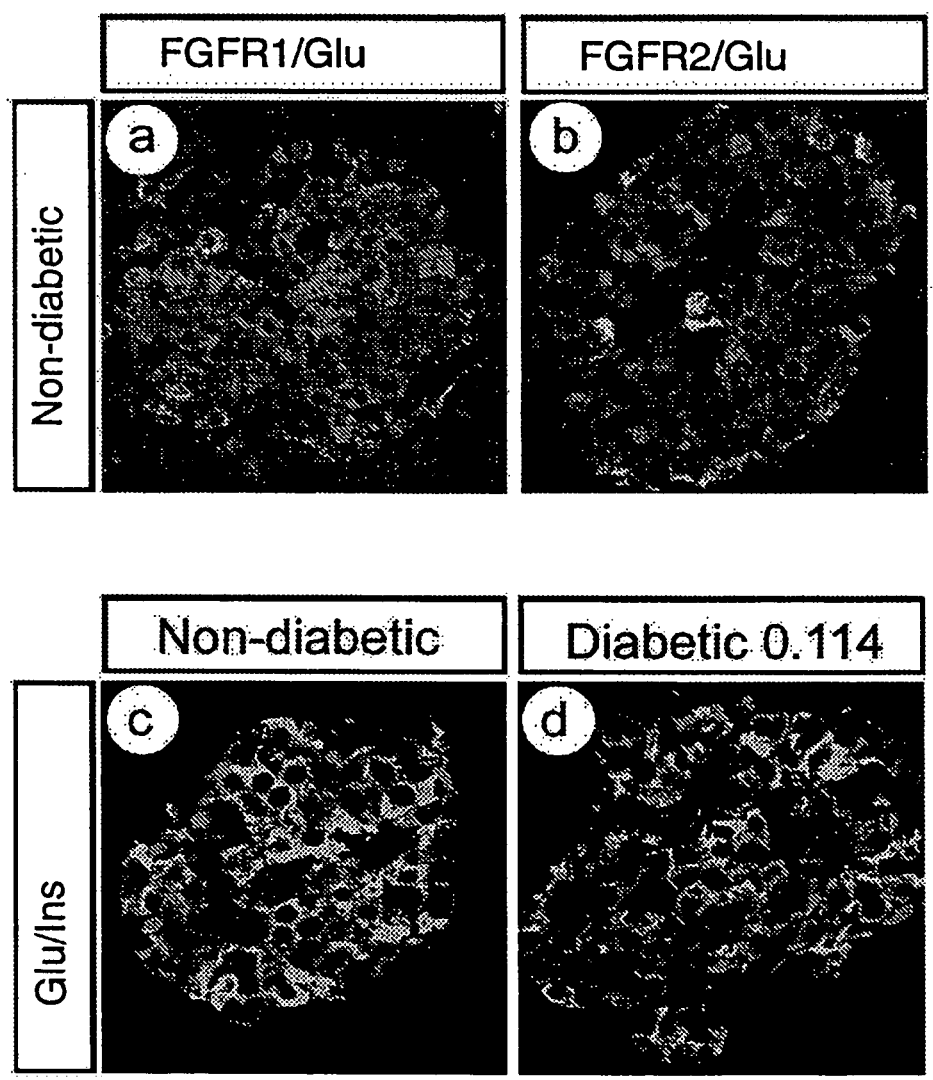

FIG. 6: Expression of FGFR1 and FGFR2 in adult human islets. Confocal microscopy analyses of FGF receptor and glucagon expression in adult human pancreas showing that the receptors FGFR1 (a) and FGFR2 (b) are expressed in □-cells and not in β-cells. The islets of human type 2 diabetic patients (n=3) (d) are disorganized with glucagon producing cells found scattered throughout the islets, as compared with non-diabetic pancreatic tissue where the glucagon cells are found at the periphery of the islet (c).

Figure 7:
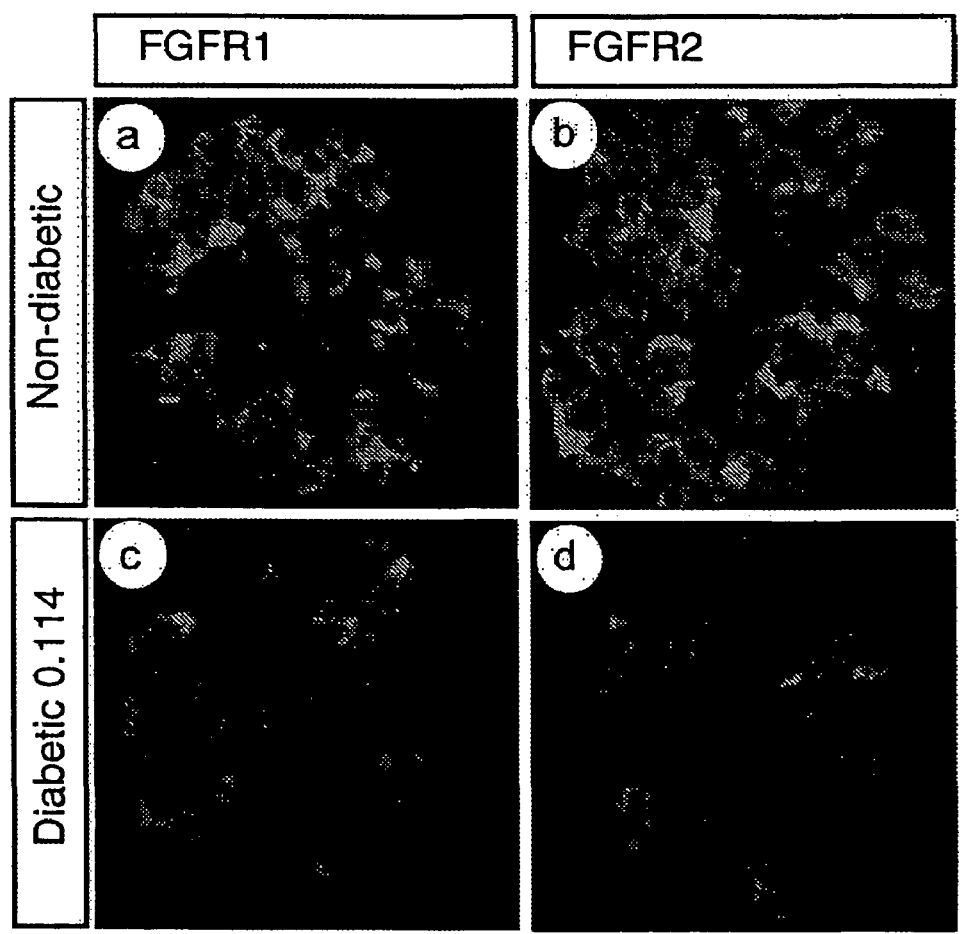

FIG. 7: Impaired expression of FGFR1 and FGFR2 in human type 2 diabetic patients. Immunohistochemical analyses demonstrate that both FGFR1 (a and c) and FGFR2 (b and d) are expressed at clearly reduced levels in β-cells of patients (n=3) suffering from type 2 diabetes. Non-diabetic pancreatic tissue (a and b), diabetic pancreatic tissue (c and d).

Figure 8:
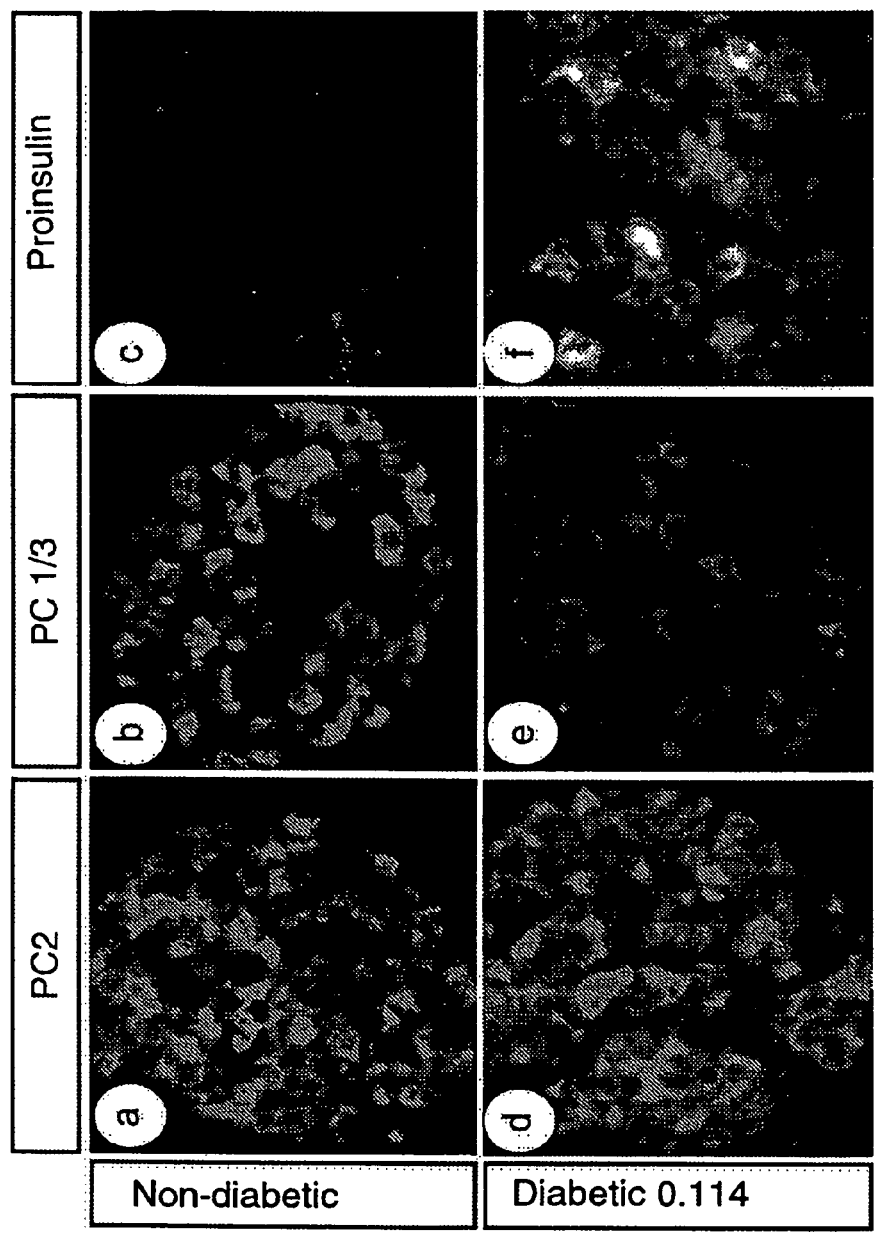

FIG. 8: Impaired expression of PC1/3 in human type 2 diabetic patients. Immunohistochemical analyses show that PC2 (a and d) expression is unaffected in human type 2 diabetic patients (n=3), whereas expression of PC1/3 (b and e) is drastically reduced. The down-regulation of PC1/3 expression leads to functional impairment of insulin processing as revealed by the increase in intracellular proinsulin content (c and f). Non-diabetic pancreatic tissue (a–c), diabetic pancreatic tissue (d–f).

Figure 9:
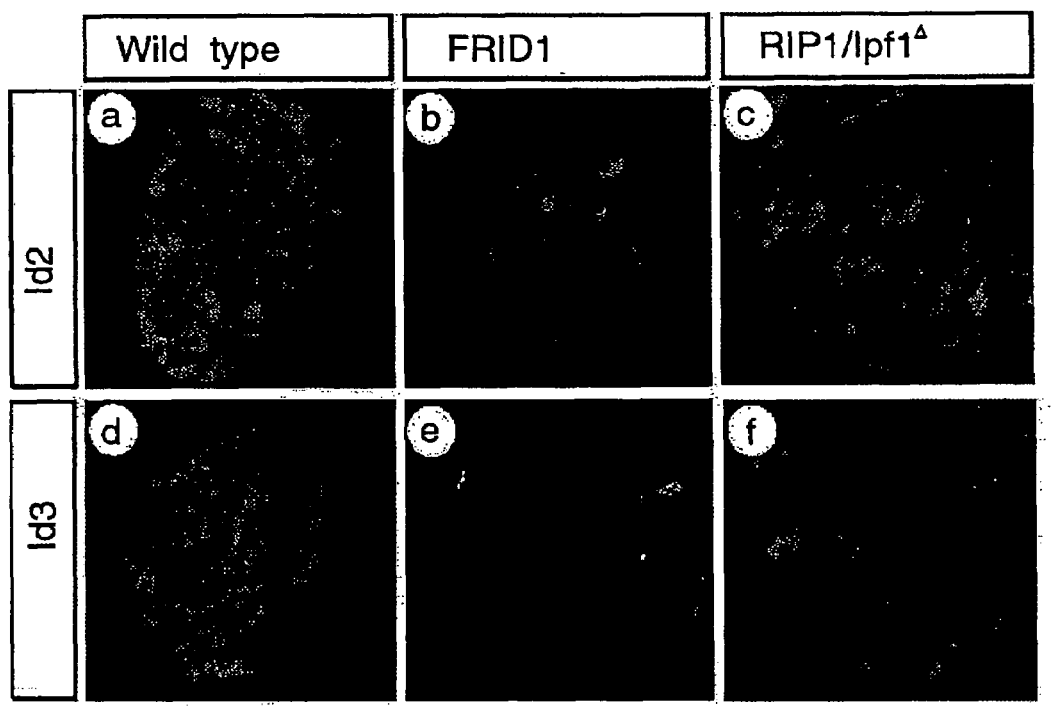

FIG. 9: Id2 and Id3 are downstream of FGFR1c-signalling. Id2 and Id3 down-regulated in β-cells of overt diabetic FRID1 and RIP1/Ipf1$^\Delta$ mice. Both Id2 and Id3 are normally expressed in mouse adult islets cells (a,d). The expression of Id2 (a–c) is greatly reduced in β-cells of diabetic FRID1 (b,e) and RIP1/Ipf1$^\Delta$ (e,f) mice as compared to that of wild type littermates and the expression of Id3 (d–f) virtually absent (e,f) in these diabetic mouse models. The remaining Id2 and Id3 expression still observed in both the FRID1 and RIP1/Ipf1$^\Delta$ islets represent expression in scattered glucagon cells.

DESCRIPTION OF PREFERRED EMBODIMENTS

EXAMPLE 1

Expression of FGFR1 in the Adult Pancreas

Analysis of FGFR1 expression in the adult mouse pancreas revealed that FGFR1 is predominantly expressed in the adult β-cell, with no expression observed in the glucagon-producing α-cells (FIG. 1). A lower level of FGFR1 expression was also observed in the exocrine cells of the pancreas (data not shown). FGFR2 is also selectively expressed in the adult β-cells but in contrast to FGFR1, FGFR2 expression was not observed in the exocrine cells of the adult pancreas (data not shown). The expression of FGFR in adult β-cells suggests a role for FGF-signalling in terminal differentiation and/or maturation of these cells.

The expression of FGFR1 in the pancreas led us to examine whether signalling via this receptor may be required for pancreas development, as has already been implied for FGFR2b. We also examined whether FGF receptor signalling was required for the specification and differentiation of adult β-cells. To begin to address this issue we generated transgenic mice expressing dominant negative FGFR1c construct in the pancreas using the Ipf1/Pdx1 promoter. This consisted of the three loop extracellular domain of FGFR1c fused in frame with the rat IgG Fc region. In the resulting mice Ipf1-expressing cells would secrete the hybrid protein from the cell allowing competitive binding of FGF ligands such as FGF1, FGF2, FGF4, FGF5 and FGF6 which are known to bind to the FGFR1c variant.

EXAMPLE 2

Development Diabetes in Ipf1/dnFGFR1c Mice.

Ipf1/dnFGFR1c express high levels of the transgene in β-cells with lower levels of the transgene being expressed in the exocrine part of the pancreas (FIG. 1 and data not shown). The Ipf1/dnFGFR1c transgenic mice are viable and fertile with a grossly well developed pancreas, providing evidence that signalling via FGFR1c is not important for pancreas growth, morphogenesis and differentiation. The mice appeared healthy until approximately 15 weeks of age when elevated non-fasting urine glucose concentrations greater than 2% were observed suggesting a diabetic phenotype. Fasting blood glucose measurements on mice were >20 mM, confirming that these animals were severely diabetic.

Close monitoring of urine and blood glucose levels revealed that already at 3 weeks of age Ipf1/dnFGFR1c mice showed elevated glucose levels, albeit still within the normal range (Table 1). At six weeks of age their fasting blood glucose levels had increased by 1 mM and they had detectable levels of glucose in their urine when compared to wild type age matched littermates (Table 1). Weekly monitoring of the urine glucose revealed a steady increase in glucose and by the age of 9–12 weeks urine glucose levels were in excess of 2%. Non-fasting and fasting blood glucose measurements taken at this stage revealed 4-fold higher glucose levels compared with age-matched wild type littermates (Table 1). These findings demonstrate that impaired FGFR1c-signaling in adult β-cells results in the development of diabetes and points to a crucial, hitherto unknown role for FGF-signalling in β-cell glucose homeostasis.

TABLE 1

Ipf1/dnFGFR1c transgenic mice develop diabetes

| | Blood glucose levels (mM +/− S.E.M.) | |
|---|---|---|
| | non-fasted | fasted |
| Wild type (3 weeks old) | nd | 4.4 +/− 0.4 (n = 5) |
| Ipf1/dnFGFR1c (3 weeks old) | nd | 5.8 +/− 0.5 (n = 7) |
| Wild type (6 weeks old) | nd | 4.9 +/− 0.3 (n = 5) |
| Ipf1/dnFGFR1c (6 weeks old) | nd | 6.8 +/− 0.8 (n = 7) |
| Wild type (12 weeks old) | 8.7 +/− 0.8 (n = 5) | 4.0 +/− 0.6 (n = 5) |
| Ipf1/dnFGFR1c (12 weeks old) | 26.4 +/− 1.5 (n = 5) | 15.8 +/− 1.3 (n = 7) |

Legend to Table 1: Blood glucose levels were measured in Ipf1/dnFGFR1c mice and wild type littermates at the time points shown. At 3 weeks of age Ipf1/dnFGFR1c mice showed non-fasted blood glucose levels within the normal range. Six-week old Ipf1/dnFGFR1c mice had slightly elevated non-fasted blood glucose levels, still within the normal range albeit at the upper level. Overt diabetes (OD) develops in 9–12 weeks old mice in whom both non-fasted and fasted blood glucose levels were 4-fold higher than wild type, age-matched littermates.

EXAMPLE 3

Demonstration of Disorganized Islets with Reduced Numbers of β-cells in Ipf1/dnFGFR1c Mice The overtly normal development of the pancreas in Ipf1/dnFGFR1c mice homozygous mutants suggested that the growth and differentiation of the pancreas is independent of FGFR1c-signaling. To assess this further we analyzed the expression of the transcription factors Isl1, Ipf1/Pdx1, Nkx6.1 and Nkx2.2, the endocrine hormones insulin (Ins), glucagon (Glu), somatostatin (Som), and the exocrine enzymes amylase and carboxypeptidase A. Each of these markers were expressed in the pancreas of Ipf1/dnFGFR1c mice and the organization of endocrine cells into islet-like clusters and of exocrine cells into acinar-like structures appeared normal (Data not shown). Nevertheless, as revealed by double immunohistochemical analysis, there was a 35% decrease in the total number of Isl1$^+$ cells paralleled by ~30% net decrease in the number of Ins$^+$-cells and a concomitant 20% increase in the relative number of Glu$^+$-cells (FIG. 2). These results suggest that the genesis and/or survival of β-cells partly depends on FGFR1c-signalling. Tunnel assays failed, however, to detect any increased β-cell apoptosis suggesting that the decreased number of β-cells are not caused by β-cell death (data not shown). The 30% decrease in total number of insulin cells in the transgenic mice was reflected by a 28% decrease in total pancreatic insulin content (FIG. 2). Moreover, although islets form in the Ipf1/dnFGFR1c mice the typical structure of maturing islets with α-cells at the periphery surrounding a core of β-cells is perturbed; instead, Glu$^+$ cells are found scattered throughout the islets (FIG. 3). In combination these histological analyses support the idea that the development of the pancreas to generate both exocrine and endocrine cells is unaffected despite the expression of a dn form of FGFR1c during pancreas development and in the adult β-cell. In addition these results provide evidence of the genesis of pancreatic β-cells appearing to be partly dependent on, and that normal organization of islet-cells requires, FGFR1c-signaling.

EXAMPLE 4

Down-Regulation of Glucose Transporter Type 2 is in Ipf1/dnFGFR1c Mice

The decrease in total insulin production by 28% appears unlikely to be sufficient to cause the diabetes observed in the transgenic mice and suggests that additional complications underlie the development of the diabetic phenotype observed in the Ipf1/dnFGFR1c mice. To determine whether other key characteristics of the adult β-cells were affected in the transgenic mice we next monitored the expression of factors crucially required for normal glucose homeostasis. Glut2 is a key component in glucose sensing machinery within the β-cell. Analyses revealed that the expression of Glut2 was virtually lost in overt diabetic Ipf1/dnFGFR1c mice (FIG. 3). To exclude that the loss of Glut2 expression was a consequence of the hyperglycemic state rather than a direct effect of the Ipf1/dnFGFR1c transgene expression, 5-week old, prediabetic transgenic mice were analyzed. Prediabetic, 5 week old Ipf1/dnFGFR1c mice exhibit a clearly reduced level of Glut2 expression as compared to wild type (not shown). These results indicate that the reduction of Glut2 expression observed in Ipf1/dnFGFR1c mice is a direct consequence of impaired FGFR1c signalling.

EXAMPLE 5

Down-Regulation of PC1/3 in Ipf1/dnFGFR1c Mice

Although the loss of Glut2 may be sufficient to cause their diabetic phenotype, the severity of the ensuing hyperglycemia in a short period of time suggested that there might be additional defects in the β-cell of Ipf1/dnFGFR1c mice. Type 2 diabetes patients and animal models of the disease, often suffer from hyperproinsulinemia, reflecting an impaired processing of proinsulin to mature, active insulin which is believed to be a major contributing factor to their disease. To elucidate a potential processing defect in the Ipf1/FGFR1dn mice we performed an immunohistochemical analysis for investigating the expression of the proinsulin processing enzymes, PC1/3 and PC2. PC1/3 expression was found to be severely down-regulated so as to be virtually absent in the Ipf1/dnFGFR1c mice, whereas only a minor decrease was observed with respect to PC2 expression in overt diabetic mice (FIG. 3 and data not shown).

Next we wanted to determine whether this aberrant processing enzymes expression could be directly involved in the development of the diabetic phenotype in the Ipf1/dnFGFR1c mice. To this effect pancreas from five-week old prediabetic and wild type littermates were analyzed for PC1/3 and PC2 expression. The analyses showed that already at 5-weeks of age expression levels of the prohormone convertases was reduced in the Ipf1/dnFGFR1c mice as compared to controls (not shown). Together, these results suggest that FGFR1c signaling is required for high level expression of PC1/3, and to a lesser extent for PC2 expression.

EXAMPLE 6

Demonstration of impaired Proinsulin Processing in

Ipf1/dnFGFR1c Mice

To address whether the impaired expression of the processing enzymes might affect insulin processing in the Ipf1/dnFGFR1c mice we examined the type of insulin made and stored in the β-cells. An antibody directed against intact human proinsulin, which do not cross-react with active insulin (Madsen et al., 1983; Madsen et al., 1984; Furuta et al., 1998), and antibodies directed against mouse C-peptide 1 and 2 (Blume et al., 1992) were used to evaluate the forms of insulin present in the β-cells of Ipf1/dnFGFR1c mice.

There was a marked reduction in the levels of both C-peptide 1 and C-peptide 2 in the β-cells of the overt diabetic transgenic mice as compared to β-cells of wild type mice (FIG. 4). In contrast, high levels of proinsulin was observed in the β-cells of the transgenic mice while no or very little proinsulin was observed in the wild type β-cells (FIG. 4). Notably increased proinsulin levels were manifest already at the prediabetic 5-week stage (data not shown). These results indicate that the down regulation of the processing enzyme, PC1/3 in the Ipf1/dnFGFR1c mice results in an impaired processing of proinsulin to its active mature form. This processing defect is likely to contribute to the development of severe diabetes in the Ipf1/dnFGFR1c mice. Thus impaired signaling via FGFR1c in the adult β-cell leads to both aberrant glucose sensing and impaired insulin processing that together ultimately progress to diabetes development.

EXAMPLE 7

Demonstration that Ipf1/Pdx1 is Required for the

Expression of FGFR1 and FGFR2

The disorganisation of islets and the down-regulation of Glut2 observed in the Ipf1/dnFGFR1c mice resembles the islet phenotype associated with a β-cell specific activation of the transcription factor Ipf1/Pdx1 demonstrated in the RIP1$^\Delta$/Ipf1 mice previously established in our laboratory (Ahlgren et al., 1998). These mice develop diabetes at 10–15 weeks of age due to a Cre-mediated excision exon 2 of the Ipf1/Pdx1 gene. Analysis of pancreas derived from RIP1$^\Delta$/Ipf1 mice showed that the expression of FGFR1 and FGFR2 was down-regulated in the β-cells (FIG. 5 and data not shown). Some residual expression could still be observed which probably reflects a residual Ipf1 expression in some of the β-cells, since these mice develop diabetes at a stage when approximately 20% of the β-cells still express Ipf1 (Ahlgren et al., 1998). To investigate whether the decrease in FGFR1c expression in the RIP1$^\Delta$/Ipf1 mice might lead to a perturbed insulin processing we performed an analysis of the expression of the prohormone convertases in the RIP1$^\Delta$/Ipf1 mice. PC1/3 was severely down-regulated in these mice as well (FIG. 5). The RIP1$^\Delta$/Ipf1 mice also displayed an increased proinsulin content in their β-cells coupled with a decreased levels of C-peptide 1 and 2 (FIG. 5, and data not shown).

In combination these results provide evidence that Ipf1 is required for the expression of FGFR1 in the adult β-cells, thereby ensuring a high level of Glut2 and PC1/3 expression. Thus, both perturbed Ipf1 expression and impaired signalling via FGFR1c leads to diabetes due to impaired glucose sensing and insulin processing in the adult β-cells with diabetes manifestation as a consequence. These results suggest that signalling via FGFR1c is critical for the maintenance of a mature, functional β-cell phenotype, and that Ipf1/Pdx1 by virtue of its key role in controlling, directly or indirectly, many aspects of the β-cell glucose homeostasis machinery is pivotal for the β-cell's capacity to preserve normoglycemia.

EXAMPLE 8

Analysis of Pancreas from Diseased Type 2

Diabetics and Control Individuals

Double immunohistochemical analyses of pancreas derived form non-diabetic humans show that both FGFR1 and FGFR2 are selectively expressed also in human insulin-producing β-cells and not glucagon producing α-cells (FIG. 6a and 6b). Similar to mice with diabetes due to impaired FGFR1-signalling [5,6], type 2 diabetics display disorganized islets with glucagon-producing α-cells mixed with the insulin-producing β-cells (FIG. 6d), whereas non-diabetics have normal islets with glucagon-producing cells surrounding the core of insulin-producing β-cells (FIG. 6c).

Moreover, the expressions of both FGFR1 and FGFR2 are drastically reduced in the insulin-producing β-cells of type 2 diabetics as compared to that of control individuals (FIG. 7). Consequently, as has been shown for mice with impaired FGFR1 signalling, type 2 diabetics show reduced expression of PC1/3 in their β-cells (FIG. 8b, 8e) whereas the expression of PC2 appear less affected (FIG. 8a, 8d). The reduction of PC1/3 expression is paralleled by an increase in β-cell proinsulin content in the Type 2 diabetics as compared to the control individuals (FIG. 8c, 8f).

These experiments demonstrate that β-cells of type 2 diabetic patients have disorganized islets, reduced expression of FGFR1, FGFR2 and PC1/3 as well as an increased proinsulin content in their β-cells. These findings when combined provide evidence that, similar to mice with diabetes due to an impaired FGFR1-signalling in adult β-cells, attenuation of FGFR1-signalling pathway in human β-cells is coupled to diabetes. We suggest that FGF-signalling in the adult pancreas ensures a functional β-cell identity and glucose homeostasis. Thus an impaired expression, or activity, of components within the FGF-signalling pathway is coupled to diabetes in both mice and humans. In both mice and humans impaired FGF-expression and signalling is coupled to a decrease in PC1/3 expression. The decrease in PC1/3 in turn leads to a perturbed processing of insulin with elevated pro insulin levels as a result. Consequently the FGF-signalling pathway, i.e. including components upstream and downstream of the FGFR-ligand interaction, is a suitable target for the development of new therapies to cure diabetes.

We have also recent data from analyses of expression of Id-proteins [Norton, 2000] that Id2 and Id3 are targets downstream of FGFR1-signalling. As is shown in FIG. 9, both Id2 and Id3 are normally expressed in pancreatic endocrine cells (FIG. 9a, 9d). However, in mice with diabetes due to attenuation of FGF-signalling in β-cells, i.e. the FRID1 and RIP1/Ipf1$^\Delta$ mice, the expression of both Id2 (FIG. 9b, 9c) and Id3 (FIG. 9e, 9f) are severely down-regulated. These results provide evidence that Id2 and Id3 expression in β-cells are dependent of FGF-signalling and hence represent downstream components of the FGF-signalling pathway in adult β-cells. Id2 and Id3 thus represent candidate targets for the development of new therapies to cure diabetes.

FIGURE LEGENDS

FIG. 1: (A–F) Analysis of FGFR1 expression in adult pancreas showing that FGFR1-expression (B, D) coincides with insulin (C) but not glucagon (A) expression. (E, F) In Ipf1/dnFGFR1c transgenic mice the dnFGFR1c protein (F) is highly expressed in IPF1$^+$ cells (E) as detected by antibodies against the Rat IgG Fc region that is coupled to the dnFGFR1c domain.

FIG. 2: (A) Analysis of number Ins$^+$-cells over number of Isl1$^+$-cells showing a 30% decrease in the number of Ins$^+$-cells in Ipf$^1$/dnFGFR$^1$c (TG) mice as compared to wild-type (wt) mice. Data from at least 4 independent mice, n=7435 cells. (B) Measurement of total pancreatic insulin content (μg insulin/mg pancreas protein) from non-fasted animals (n=6 wt and n=8 TG) show that the 30% decrease in number of Ins$^+$-cells (A) is accompanied by a 28% decrease in total pancreatic insulin content in the Ipf1/dnFGFR1c mice as compared with their age-matched wild type littermates. (C) The 30% decrease in number of insulin cells results in a relative 20% increase in number of Glu$^+$-cells in Ipf$^1$/dnFGFR$^1$c mice. Data from at least 4 independent mice, n=7525 cells.

FIG. 3: (A–D) Confocal microscopy analyses of insulin (C,D) and glucagon (A,B) expression in wild-type (A,C) and Ipf$^1$/dnFGFR1c transgenic (B,D) mice show that the islet organisation in the transgenic mice is abnormal but that there is no co-expression between insulin and glucagon within the islet cells. (E–H) Expression of glucose sensing and insulin processing enzymes is impaired in Ipf1/dnFGFR1c mice. Images show that Glut2-expression (E,F) in adult β-cells is lost as a result of Ipf1/dnFGFR1c expression and that only a very low level of PC3 expression (G,H) remains in Ipf1/dnFGFR1c mice, and preferentially in α-cells.

FIG. 4: Analyses of insulin variants in pancreas from wild-type (A, C, E, G) and Ipf1/dnFGFR1c (B, D, F, H) mice using C-peptide 1 (A and B), C-peptide 2 (C and D), insulin (E and F) and proinsulin (G and H) anti-sera. (A, C, E, G) In wild-type pancreas insulin is present predominantly in its fully processed form (A, C, E) with virtually no detectable unprocessed pro-insulin (G). Note that the fluorescence in C represents background, non-β-cell reactivity due to the use of mouse monoclonal anti-sera. (B, D, F, H) Ipf1/dnFGFR1c mice display a perturbed proinsulin processing resulting in reduction of fully processed insulin (B, D, F) while a substantial, readily detectable fraction remains in the form of proinsulin (H).

FIG. 5: (A–F) Loss of IPF1/PDX1 activity in β-cells (Ahlgren et al. 1998) results in a drastically reduced FGFR1 (A,B) and PC3 (C,D) expression. This loss of PC3 expression results in perturbed proinsulin processing, with a reduction in detectable levels of fully processed insulin (not shown) accompanied by increased levels of detectable pro-insulin (E,F) within the β-cells of the Rip1/Ipf1$^Δ$ mice (B,D,F) as compared to wild-type littermates (A,C,E).

FIG. 6: Expression of FGFR1 and FGFR2 in adult human islets. Confocal microscopy analyses of FGF receptor and glucagon expression in adult human pancreas showing that the receptors FGFR1 (a) and FGFR2 (b) are expressed in □-cells and not in β-cells. The islets of human type 2 diabetic patients (n=3) (d) are disorganized with glucagon producing cells found scattered throughout the islets, as compared with non-diabetic pancreatic tissue where the glucagon cells are found at the periphery of the islet (c).

FIG. 7: Impaired expression of FGFR1 and FGFR2 in human type 2 diabetic patients. Immunohistochemical analyses demonstrate that both FGFR1 (a and c) and FGFR2 (b and d) are expressed at clearly reduced levels in β-cells of patients (n=3) suffering from type 2 diabetes. Non-diabetic pancreatic tissue (a and b), diabetic pancreatic tissue (c and d).

FIG. 8: Impaired expression of PC1/3 in human type 2 diabetic patients. Immunohistochemical analyses show that PC2 (a and d) expression is unaffected in human type 2 diabetic patients (n=3), whereas expression of PC1/3 (b and e) is drastically reduced. The down-regulation of PC1/3 expression leads to functional impairment of insulin processing as revealed by the increase in intracellular proinsulin content (c and f). Non-diabetic pancreatic tissue (a–c), diabetic pancreatic tissue (d–f).

FIG. 9: Id2 and Id3 are downstream of FGFR1c-signalling. Id2 and Id3 down-regulated in β-cells of overt diabetic FRID1 and RIP1/Ipf1$^Δ$ mice. Both Id2 and Id3 are normally expressed in mouse adult islets cells (a,d). The expression of Id2 (a–c) is greatly reduced in β-cells of diabetic FRID1 (b,e) and RIP1/Ipf1$^Δ$ (e,f) mice as compared to that of wild type littermates and the expression of Id3 (d–f) virtually absent (e,f) in these diabetic mouse models. The remaining Id2 and Id3 expression still observed in both the FRID1 and RIP1/Ipf1$^Δ$ islets represent expression in scattered glucagon cells.

REFERENCES

Ahlgren U, Jonsson J, Jonsson L, Simu K, Edlund H (1998). β-cell-specific inactivation of the mouse Ipf1/Pdx1 gene results in loss of the beta-cell phenotype and maturity onset diabetes. Genes Dev 12, 1763–8.

Apelqvist A, Ahlgren U, Edlund H (1997). Sonic hedgehog directs specialised mesoderm differentiation in the intestine and pancreas. Curr Biol 7:801–4.

Blume N, Petersen J S, Andersen L C, Kofod H, Dyrberg T, Michelsen B K, Serup P, Madsen O D. (1992). Immature transformed islet b-cells differentially express C-peptides derived from genes coding for insulin I and II as well as a transfected human insulin gene. Mol Endocrinol 6:299–307.

Campochiaro P A, Chang M, Ohsato M, Vinores S A, Nie Z, Hjelmeland L, Mansukhani A, Basilico C, Zack D J (1996). Retinal degeneration in transgenic mice with photoreceptor-specific expression of a dominant-negative fibroblast growth factor receptor. J Neurosci 16, 1679–88.

Celli G, LaRochelle W J, Mackem S, Sharp R, Merlino G (1998). Soluble dominant-negative receptor uncovers essential roles for fibroblast growth factors in multi-organ induction and patterning. EMBO J 17, 1642–55.

De Moerlooze L, Spencer-Dene B, Revest J, Hajihosseini M, Rosewell I, Dickson C (2000). An important role for the IIIb isoform of fibroblast growth factor receptor 2 (FGFR2) in mesenchymal-epithelial signalling during mouse organogenesis. Development 127, 483–92.

Furuta M, Carroll R, Martin S, Swift H H, Ravazzola M, Orci L, Steiner D F (1998). Incomplete processing of proinsulin to insulin accompanied by elevation of Des-31,32 proinsulin intermediates in islets of mice lacking active PC2. J Biol Chem 273:3431–7

Haffner S M, Gonzalez C, Mykkanen L, Stern M (1997). Total immunoreactive proinsulin, immunoreactive insulin and specific insulin in relation to conversion to NIDDM: the Mexico City Diabetes Study. Diabetologia, 40:830–7.

Hani E H, Stoffers D A, Chevre J C, Durand E, Stanojevic V, Dina C, Habener J F, Froguel P (1999). Defective mutations in the insulin promoter factor-1 (IPF-1) gene in late-onset type 2 diabetes mellitus. J Clin Invest 104: R41–48.

Hales C N (1994). The pathogenesis of NIDDM. Diabetologia 37 Suppl 2, S162–8.

Itoh N, Mima T, Mikawa T (1996). Loss of fibroblast growth factor receptors is necessary for terminal differentiation of embryonic limb muscle. Development, 122, 291–300.

Kahn B B (1998). Type 2 diabetes: when insulin secretion fails to compensate for insulin resistance. Cell 92:593–6.

Kahn B B, Rossetti L (1998). Type 2 diabetes—who is conducting the orchestra? Nat Genet 20:223–5.

Kahn S E, Leonetti D L, Prigeon R L, Boyko E J, Bergstrom R W, Fujimoto W Y (1995). Proinsulin as a marker for the development of NIDDM in Japanese-American men. Diabetes 44:173–9. Kahn S E et al. (1995). Proinsulin as a marker for the development of NIDDM in Japanese-American men. Diabetes 44: 173–179.

Kahn S E et al. (1995). Relationship of proinsulin and insulin with noninsulin-dependent diabetes mellitus and coronary heart disease in Japanese-American men: impact of obesity—clinical research center study. J Clin Endocrinol Metab 80: 1399–1406.

Kato S, Sekine K (1999). FGF-FGFR signaling in vertebrate organogenesis. Cell Mol Biol 45:631–8.

Krakowski M L, Kritzik M R, Jones E M, Krahl T, Lee J, Arnush M, Gu D, Sarvetnick N (1999). Pancreatic expression of keratinocyte growth factor leads to differentiation of islet hepatocytes and proliferation of duct cells. Am J Pathol 154:683–91.

Larsson H, Ahren B (1999). Relative hyperproinsulinemia as a sign of islet dysfunction in women with impaired glucose tolerance. J Clin Endocrinol Metab 84:2068–74.

Le Bras S, Miralles F, Basmaciogullari A, Czernichow P, Scharfmann R (1998). Fibroblast growth factor 2 promotes pancreatic epithelial cell proliferation via functional fibroblast growth factor receptors during embryonic life. Diabetes 47, 1236–42.

Macfarlane W M, Frayling T M, Ellard S Evans J C, Allen L I, Bulman M P, Ayres S, Shepherd M, Clark P, Millward A, Demaine A, Wilkin T, Docherty K, Hattersley A T (1999). Missense mutations in the insulin promoter factor-1 gene predispose to type 2 diabetes. J Clin Invest 104:R33–39.

Madsen O D, Cohen R M, Fitch F W, Rubenstein A H, Steiner D F (1983). The production and characterization of monoclonal antibodies specific for human proinsulin using a sensitive microdot assay procedure. Endocrinology 113: 2135–2144.

Madsen O D, Frank B H, Steiner D F (1984). Human proinsulin-specific antigenic determinants identified by monoclonal antibodies. Diabetes 33:1012–1016.

Miralles F, Czernichow P, Ozaki K, Itoh N, Scharfmann R (1999). Signaling through fibroblast growth factor receptor 2b plays a key role in the development of the exocrine pancreas. Proc Natl Acad Sci U S A 96, 6267–72.

Mykkänen L, Haffner S M, Kuusisto J, Pyorala K, Hales C N, Laakso M (1995). Serum proinsulin levels are disproportionately increased in elderly prediabetic subjects. Diabetologia 38:1176–82.

Mykkänen L, Haffner S M, Hales C N, Ronnemaa T, Laakso M (1997). The relation of proinsulin, insulin, and proinsulin-to-insulin ratio to insulin sensitivity and acute-insulin-response in normoglycemic subjects. Diabetes 46:1990–5.

Mykkanen L, Zaccaro D, Hales C N, Festa A, Haffner S M (1999). The relation of proinsulin and insulin to insulin sensitivity and acute insulin response in subjects with newly diagnosed type II diabetes: the Insulin Resistance Atherosclerosis Study. Diabetologia 42:1060–1066.

Nguyen H Q, Danilenko D M, Bucay N, DeRose M L, Van G Y, Thomason A, Simonet W S (1996). Expression of keratinocyte growth factor in embryonic liver of transgenic mice causes changes in epithelial growth and differentiation resulting in polycystic kidneys and other organ malformations. Oncogene 12, 2109–19.

Nijpels G, Popp-Snijders C, Kostense P J, Bouter L M, Heine R J (1996). Fasting proinsulin and 2-h post-load glucose levels predict the conversion to NIDDM in subjects with impaired glucose tolerance: the Hoorn Study. Diabetologia 39:113–8.

Norton J D (2000). ID helix-loop-helix proteins in cell growth, differentiation and tumorigenesis. J Cell Sci. 113: 3897–3905.

Ohlsson H, Karlsson K, Edlund T (1993). IPF1, a homeodomain-containing transactivator of the insulin gene. Embo J 12: 4251–4259.

Porte D Jr, Kahn S E. Hyperproinsulinemia and amyloid in NIDDM (1989). Clues to etiology of islet beta-cell dysfunction? Diabetes 38:1333–6.

Rachman J, Levy J C, Barrow B A, Manley S E, Turner R C (1997). Relative hyperproinsulinemia of NIDDM persists despite the reduction of hyperglycemia with insulin or sulfonylurea therapy. Diabetes 46:1557–1562.

Stoffers D A, Ferrer J, Clarke W L, Habener J F (1997). Early-onset type-II diabetes mellitus (MODY4) linked to IPF1. Nat Genet 17:138–139.

Szebenyi G, Fallon J F (1999). Fibroblast growth factors as multifunctional signaling factors. Int Rev Cytol 185: 45–106.

Taylor S I (1999). Deconstructing type 2 diabetes. Cell 97:9–12.

Ye W, Shimamura K, Rubenstein J L, Hynes M A, Rosenthal A (1998). FGF and Shh signals control dopaminergic and serotonergic cell fate in the anterior neural plate. Cell 93, 755–66.

The invention claimed is:

1. A transgenic diabetes type II model laboratory mouse comprising β-cells expressing a dominant negative form of fibroblast growth factor receptor 1c (FGFR1c) wherein the expression of the dominant negative form of FGFR1c is controlled by a Ipf1/Pdx1 promoter, and the dominant negative form of FGFR1c is expressed by a transgene incorporated into the genome of the mouse.

2. Isolated mouse β-cells having been genetically modified to express a dominant negative form of FGFR1c wherein the expression of the dominant negative form of FGFR1c is controlled by a Ipf1/Pdx1 promoter, and the dominant negative form of FGFR1c is expressed by a transgene incorporated into the genome of the cells.

3. The β-cells of claim 2, wherein the β-cells are incompetent to express Glut2.

4. Isolated adult mouse pancreatic β-cells having been genetically modified to express a dominant negative form of FGFR1c, wherein the expression of the dominant negative form of FGFR1c is controlled by a lpf1/Pdx1 promoter, and the dominant negative form of FGFR1c is expressed by a transgene incorporated into the genome of the cells.

* * * * *